United States Patent
Schiene et al.

(10) Patent No.: US 7,675,237 B2
(45) Date of Patent: Mar. 9, 2010

(54) DIELECTRIC BARRIER DISCHARGE LAMP WITH INTEGRATED MULTIFUNCTION MEANS

(75) Inventors: Wolfgang Schiene, Aachen (DE); Georg Greuel, Roetgen (DE); Georg Friedrich Gartner, Aachen (DE); Norbert Braun, Aachen (DE); Ronald Peter Groenestein, Eindhoven (NL); Henricus Lambertus Antonius Adrianus Vogels, Lieshout (NL); Volker Dirk Hildenbrand, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 526 days.

(21) Appl. No.: 11/571,835

(22) PCT Filed: Jul. 8, 2005

(86) PCT No.: PCT/IB2005/052276
§ 371 (c)(1),
(2), (4) Date: Jan. 9, 2007

(87) PCT Pub. No.: WO2006/006139
PCT Pub. Date: Jan. 19, 2006

(65) Prior Publication Data
US 2008/0093967 A1    Apr. 24, 2008

(30) Foreign Application Priority Data
Jul. 9, 2004    (EP) .................... 04103265

(51) Int. Cl.
*H01J 11/00*    (2006.01)
*H01J 65/00*    (2006.01)
(52) U.S. Cl. .................... 313/607; 313/234; 313/634
(58) Field of Classification Search ................. 313/234, 313/607, 25, 634, 36, 573, 17, 609
See application file for complete search history.

(56) References Cited

U.S. PATENT DOCUMENTS

| | | | |
|---|---|---|---|
| 3,984,727 A * | 10/1976 | Young .................... 315/267 |
| 5,386,170 A | 1/1995 | Kogelschatz |
| 5,432,398 A | 7/1995 | Kogelschatz |
| 5,444,331 A | 8/1995 | Matsuno et al. |
| 5,666,026 A * | 9/1997 | Matsuno et al. ............ 313/634 |
| 5,763,999 A * | 6/1998 | Matsuno et al. ............ 313/573 |

(Continued)

FOREIGN PATENT DOCUMENTS

EP    1048620 B1    10/2003

(Continued)

*Primary Examiner*—Peter J Macchiarolo
*Assistant Examiner*—Glenn Zimmerman

(57) ABSTRACT

The subject of the present invention is a dielectric barrier discharge (DBD-) lamp (1) for generating and emitting an ultraviolet radiation with ignition aid comprising: a discharge gap (2) being at least partly formed and/or surrounded by at least an inner wall (5) and an outer wall (4), whereby at least one of the walls (4, 5) is a dielectric wall and at least one of the walls (4, 5) has an at least partly transparent part, a filling located inside the discharge gap (2), at least two electrical contacting means, a first mean for electrical contacting associated with the outer wall (4) and a second mean for electrical contacting associated with the inner wall (5), whereby at least one multifunctional means (3) is arranged adjacent to the discharge gap (2) functioning as guiding aid and as ignition aid.

13 Claims, 6 Drawing Sheets

U.S. PATENT DOCUMENTS

| | | | |
|---|---|---|---|
| 5,889,367 A * | 3/1999 | Hofmann et al. | 313/634 |
| 6,060,828 A | 5/2000 | Vollkommer et al. | |
| 6,297,599 B1 | 10/2001 | Dirscherl et al. | |
| 6,858,988 B1 * | 2/2005 | Laroussi | 315/111.21 |
| 2003/0111960 A1 | 6/2003 | Doll et al. | |

FOREIGN PATENT DOCUMENTS

| | | |
|---|---|---|
| JP | 08031387 A | 2/1996 |
| JP | 10275601 A | 10/1998 |
| WO | 02082488 A2 | 10/2002 |

* cited by examiner

DIELECTRIC BARRIER DISCHARGE LAMP WITH INTEGRATED MULTIFUNCTION MEANS

The present invention relates to a dielectric barrier discharge (DBD-) lamp for generating and emitting an ultraviolet radiation with ignition aid comprising: a discharge gap being at least partly formed and/or surrounded by at least an inner wall and an outer wall, whereby at least one of the walls is a dielectric wall and at least one of the walls has an at least partly transparent part, a filling located inside the discharge gap, at least two electrical contacting means, a first means for electrical contacting associated with the outer wall and a second means for electrical contacting associated with the inner wall.

Such well-known dielectric barrier discharge lamps are generally known and are used in a wide area of applications, where light waves of a certain wavelength have to be generated for a variety of purposes. Some applications are for example generating UV radiation with wavelengths of about 180 nm to 380 nm for industrial purposes such as wastewater treatment, disinfections of drinking water, dechlorination or production of ultra pure water.

Well known dielectric barrier discharge lamps are used for example in flat lamps for liquid crystal display (LCD) backlighting, as cylindrical lamps for photocopiers, and as co-axial lamps for surface and water treatment purposes.

EP 1048620B1 describes a DBD lamp, which is suited for fluid disinfection and comprises luminescent layers, in this case phosphor layers, which are deposited onto the inner surfaces of the lamp envelope, in this case made of two quartz tubes, which define a discharge volume or a discharge gap. In this case the discharge gap is filled with xenon gas at a certain pressure, which emits a primary radiation as soon as a gas discharge, especially a dielectric barrier discharge, is initiated inside the discharge gap. This primary plasma radiation with an emitting maximum of about 172 nm is transformed by the luminescent layer into the desired wavelength range for example of about 180 nm to about 380 nm. According to the specified applications, this range can be reduced to a range of 180 nm-190 nm in case of the production of ultra pure water or to a range of 200 nm-280 nm if used for disinfections of water, air, surfaces and the like.

U.S. Pat. No. 5,432,398 shows an UV excimer radiator with an ignition behaviour, that is during the initial ignition or after relatively long operating pauses improved by providing means for local field distortion in the discharge space. These means can either be local constrictions provided in a pin-pointed fashion or a disturbing body made from aluminium oxide or titanium oxide.

The drawback of this radiator is, that the means have only one function and that the improving of the initial ignition is only done by local field distortion. By providing this means in a DBD lamp, a disturbing body or local constrictions, the initial ignition is improved compared to DBD lamps having no such means. But compared to what is possible, the ignition aid according to the prior art is not optimised and still needs a high initial voltage. The reason for this high initial voltage is due to the fact, that the principle of an initial ignition based on local field distortion is still a gas discharge in this area. This means that the required initial ignition voltage $U_i$ can be described according the following formula: $U_i > U_z(p,d)$, where $U_z(p,d)$ is a function of the filling pressure p and the width d of the discharge gap in the area of the ignition aid. This function is well known as the Paschen's law and can be approximated with the following equation:

$$U_z(p \cdot d) = \frac{A \cdot p \cdot d}{B + \ln(p \cdot d)},$$

where A and B are parameters, which have to be chosen according to the gas filling inside the discharge gap.

Plotting this formula results in an U-like or parabolic graph, whereby the minimum of that U-shaped graph represents the minimal initial ignition voltage.

To reach this optimum at a constant filling pressure, a very exact positioning of the means is necessary. Ignition with a local constriction of the gap only works if the operating voltage is on the right side of the Paschen minimum. Otherwise, realization of an optimised ignition aid by means of gap constrictions is not possible. If the minimal initial voltage, which is represented by the minimum of the Paschen curve, is higher than the acceptable operating voltage or higher than the voltage a certain power supply can deliver, a reliable initial ignition especially after a long operating pause can not guaranteed at all.

It is an object of the present invention to provide multifunctional means, which on the one hand serves as an improved and optimised ignition aid, especially for initial ignition or ignition after a long pause, and on the other hand serves at least as guiding means, for easily arranging two walls towards each other and thereby forming an optimised discharge gap, especially for coaxial DBD-lamps.

This issue is addressed by a dielectric barrier discharge (DBD-) lamp for generating and/or emitting an ultraviolet radiation with integrated multifunction means comprising: a discharge gap having a filling with an internal filling pressure being at least partly formed and/or surrounded by an inner wall, an outer dielectric wall, spaced to that inner wall with a distance d defining the gap width, whereby at least one wall is made of a dielectric material and at least on of the wall is at least partly transparent, and electrical connecting means, for example electrodes, supplying electrical energy for generating a gas discharge inside the discharge gap, whereby at least one multifunctional means functioning as guiding aid and at least as initial ignition aid is arranged inside the discharge gap.

A DBD-lamp according to this invention comprises an outer part and an inner part. The outer part comprises the envelope of the inner part, whereby the inner part comprises the means for generating the radiation and the emitting light of the DBD-lamp. The inner part of a DBD-lamp according to this invention is structural arranged from the inside to the outside as follows:

The heart of the DBD-lamp is the discharge gap with the filling. This discharge gap is formed by surrounding walls, whereby at least one of these walls is made of a dielectric material and at least one of the walls is at least partly transparent. These walls may be covered at their inner surfaces with a luminescent layer, especially a luminescent coating layer for transferring the radiation generated inside the discharge gap into a radiation with a different, especially higher wavelength, which is then emitted to the surrounding of the DBD-lamp. At their outer surfaces the walls have two corresponding means for electrical contacting for supplying the energy to generate a gas discharge inside the discharge gap and thus for generating a radiation inside the discharge gap.

The material for the dielectric wall(s) is selected from the group of dielectric materials, preferably quartz, glass or ceramic. The material for the dielectric walls have to be arranged such, that the radiation can pass at least a part of the outer and/or the inner wall for applying the radiation to the surroundings of the DBD-lamp. Each wall has an inner and an outer surface. The inner surface of each wall is directed to and facing the discharge gap. The distance between the inner surface and the outer surface of one wall defines the wall thickness, which in some special cases can vary. At the outer surfaces or near the outer surfaces the means for electrical contacting are applied. They supply the energy in form of electricity for generating the gas discharge inside the discharge gap and thus generating the radiation inside the discharge gap. For applying the radiation, the electrode or electrical contacting means at/on at least one of the walls has to be arranged such, that radiation from the inside can pass the corresponding electrode. Thus said electrode preferably is arranged as a grid, especially when that electrode is arranged adjacent on the outer surface of the outer wall or on the outer surface of the inner wall. In that case, in that the electrode is spaced to the outer surface of the outer wall or to the outer surface of the inner wall, for example in the case of water treatment, the electrode can be of any suitable material for providing electricity in the corresponding environment.

Preferably the lamp geometry is selected from the group comprising flat lamp geometry, coaxial lamp geometry, dome lamp geometry, a planar lamp geometry and the like. For industrial purposes coaxial DBD-lamps with relatively large diameters compared to the diameter of the discharge gap or the distance between the inner surfaces of the corresponding inner and outer wall or dome-shaped coaxial lamps are preferably used, to achieve a lamp with a large effective area for fluid and surface treatment.

It was found, that the optimal operating (peak) amplitude of a DBD lamp, especially a highly efficient and high power DBD lamp is quite close to—sometimes even just under—the required initial ignition voltage. Therefore, additional means, like auxiliary electrodes or temporary voltage overshoot, are normally necessary to achieve a reliable lamp start-up. All these measures will lead to a more complex and thus more expensive lamp power supply or lamp driver.

One advantage of the present invention is, that by having multifunctional means functioning as guiding aid and at least as initial ignition aid inside the discharge gap several functions can be integrated in one means. By having this multifunctional means, there is no necessity to have several additional means. The means can be generally realized in two ways: first by locally limited regions having a reduced gap width d or by modification of the permittivity (dielectric constant) of the wall or discharge vessel material. Inside the discharge gap in the sense of the invention means, that the multifunctional means protrude into or from the discharge gap. By having this means, an easy arrangement of the walls towards each other is possible. Also the voltage amplitude needed for initial ignition is lower due to the multifunctional means. Other advantages are a reliable ignition, especially after long operating pauses, a simple lamp design, no auxiliary electrodes, no auxiliary discharge volumes, and the filling pressure inside the gap as well as the gap width can be optimised regarding maximal lamp efficiency.

Preferably at least one multifunctional means protrudes from one wall to the other wall with a distance t that can vary in the whole range of the discharge gap width d except a value about d/2. By having an adjustable distance t, an optimized ignition condition can be arranged.

If t is 0, the ignition aid is realized by using a material in a local area of the wall(s) that differs from the material of the rest of the walls. This material has a different electrical constant than the material for the rest of the walls, which reduces the effort for ignition.

If t equals d, the multifunctional means form a direct contact between the inner wall and the outer wall. The direct contact can be in form of a contact point, a contact line, and/or a contact area.

In case of at least one contact line, the contact line(s) may have any arbitrary shape along the inner and/or outer tube. Contact lines in parallel with the length axis of the lamp may have special advantages to provide a guidance aid, an ignition aid, and no modification of the cross sectional shape (vertical to the length axis of the lamp) is needed. The latter, is useful to provide a lamp without distortions for improved wiping.

In case of at least one contact area, the contact area(s) may have any arbitrary shape along the inner and/or outer tube. Contact areas in parallel with the length axis of the lamp may have special advantages to provide a guidance aid, an ignition aid, and no modification of the cross sectional shape (vertical to the length axis of the lamp) is needed. The latter, is useful to provide a lamp without distortions for improved wiping Due to contact line(s) and/or area(s), the generation of sub-volumes is possible. Thus, the discharge volume enclosed between outer and inner wall of the lamp is divided into two or even more sub-volumes. Each sub-volume is ignited by the surface discharge along the multifunction means directed towards the entire sub-volume.

By this, the initial ignition results not by a discharge through the gas, but rather by a kind of gliding discharge along the surface. By this contact much lower initial ignition voltage is needed. Therefore it is preferably, that the multifunctional means extends from one wall to the other wall for forming a contact between both walls. By this a guiding aid and an ignition aid is realized simultaneously.

DBD lamps use for example a xenon gas filling for generation radiation in the VUV—or UVC range. Such lamps can be arranged for example as double tube constructions. For low power lamps with a relative short length in the range of several tens of cm, the manufacturing and mechanical stability of a double tube structure is feasible. However, for high power lamps with a long length compared to the discharge gap width d, for example having a length of more than 50 cm, the inner tube has to be arranged in relation to the outer tube, preferably centered, during manufacturing. Instead of melting glass rods, which have several drawbacks, indentations in the tube walls are made. The shape and the depth or the distance t can be well controlled and guarantees a good centering.

For functioning as guiding aid and simultaneously as ignition aid, the multifunctional means exhibit optimum performance if the gap is completely bridged. An ignition voltage lower than the working voltage is established by the activation of a surface discharge along the indentation and inside the gap. This surface discharge triggers the volume discharge if the lamp voltage is increased above the ignition threshold.

The method of manufacturing such a DBD-lamp includes the following steps:

After local heating of the glass surface, where the indentation is needed, the glass wall is pushed in with a heat resistant tool. Alternatively the indentations can also be made for example on the inner tube by pushing the glass outward. In this case the indentations will touch the outer tube on the inside.

Preferably the multifunctional means is an integral part of at least one of the walls. That means, no additional parts are needed. The multifunctional means is arranged in at least one locally limited region of the wall as a part of the wall for example as point, line, and/or ring shaped thickening on the inner wall and/or the outer wall.

One advantage is that the integral multifunctional means has about the same or a thinner wall-thickness as the corresponding wall, whereby the changeover from wall to multifunctional means is smooth. By this an optimized ignition aid is realized. Due to the discharge at the surface of the walls along the surface of the multifunctional means a better ignition with lower energy compared to ignition aid by local field distortion is realized. By ignition aid with local field distortion the distance d is calculated according to Paschen's law. If the minimum of the Paschen curve for a given gas filling pressure of a DBD lamp is still above the working voltage of said lamp, there is no possibility of reducing the required ignition voltage by local gap reduction with a residual finite gap width. By realizing a discharge at the surface of the walls, the equipotent lines of the electric field are bended/modified such that an essential reduction of the required initial ignition voltage is realized. The required initial ignition voltage is essentially lower than the minimum of the corresponding Paschen curve. The previously mentioned is optimized by having a wall thickness in the area of the contact that is not larger than the wall thickness of the walls.

Preferably at least two multifunctional means are protruding into/from the discharge gap spaced perpendicular and/or axially to the longitudinal axis. By this an optimized guiding aid is realized and several areas are formed as ignition aid that makes ignition easier.

More preferably three multifunctional means are arranged. By that a very exact working guiding aid is realized. In case of a discharge gap formed by two cylinders the means can be located along one circumferential line of the cylinders, for example spaced at a degree of 120°. The multifunctional means could also be spaced axially.

The multifunctional means can have any form. Preferably, the multifunctional means is tooth-like or sinus-like formed with smooth changeovers. This form is easy to produce and gives good results for ignition aid. Having a discharge gap formed by two cylinders, the form of the discharge gap is annular shaped. To arrange the inner cylinder precisely, several multifunctional means are needed.

Preferably the multifunctional means are all formed the same to have the inner cylinder coaxial arranged with regard to the outer cylinder. In this case the inner cylinder or tube can be accurately arranged with regard to the outer cylinder or tube.

Serving as a guiding means, the multifunctional means at least form one contact point, contact line, and/or contact area between inner and outer wall. This area will also be used for ignition of the gas discharge, due to reduced required ignition voltage amplitude. In the contact area, the equipotential lines of the electrical field are modified such, that they are directed through the wall of the multifunctional means, thus initiating a gliding discharge at the surface of the glass wall which in turn will ignite the gap discharge.

Although the DBD lamp can have any form, it is preferred, that the walls are formed by two coaxial cylinder quartz tubes melted together on both side, thus forming an annular discharge gap. This produces a good relation between surface area and discharge volume of the DBD-lamp.

Preferably the multifunctional means are located and spaced circumferentially and/or axially at the inner surface of one of the walls. More preferably the multifunctional means are arranged of a material different to the material of the walls, preferably of a material having a different electrical characteristic. One electrical characteristic is for example the dielectric constant $\in_r$. Preferably the dielectric constant is in the range $>=1.0$ to $<=10.0$, more preferably $>=2.0$ to $<=9.0$, and most preferably $>=2.5$ to $<=8.0$. Preferably the dielectric constant of the multifunctional means is higher than the dielectric constant of the walls.

The DBD-lamp according to the invention can be used in a wide area of applications. Preferably the lamp is used in a system incorporating a lamp according to any of the Claims 1 to 9 and being used in one or more of the following applications: fluid and/or surface treatment of hard and/or soft surfaces, preferably cleaning, disinfection and/or purification; liquid disinfection and/or purification, beverage disinfection and/or purification, water disinfection and/or purification, wastewater disinfection and/or purification, drinking water disinfection and/or purification, tap water disinfection and/or purification, production of ultra pure water, gas disinfection and/or purification, air disinfection and/or purification, exhaust gases disinfection and/or purification, cracking and/or removing of components, preferably anorganic and/or organic compounds cleaning of semiconductor surfaces, cracking and/or removing of components from semiconductor surfaces, cleaning and/or disinfection of food, cleaning and/or disinfection of food supplements, cleaning and/or disinfection of pharmaceuticals. One advantageously application is the purification or in general the cleansing. This is mainly done by destroying unwanted microorganisms and/or cracking unwanted compounds and the like. By this essential function of that DBD-lamp the above mentioned applications can be easily realised.

These and other aspects of the invention will be apparent form and elucidated with reference to the embodiments described hereinafter.

FIG. 1 shows in a longitudinal sectional view a coaxial DBD-lamp including a discharge gap formed by two coaxial cylinders with one circumferential multifunctional means arranged as annular dent protruding from the outer wall to the discharge gap.

FIG. 2*a* shows in a longitudinal sectional view a discharge gap formed by two coaxial cylinders with one circumferential multifunctional means arranged as thickening protruding from the outer wall to the inner wall.

FIG. 2*b* shows in a longitudinal sectional view a discharge gap formed by two coaxial cylinders with one circumferential multifunctional means arranged as thickening protruding from the inner wall to the outer wall.

FIG. 3*a* shows in a longitudinal sectional view a discharge gap formed by two coaxial cylinders with one circumferential multifunctional means arranged as dent protruding from the outer wall to the inner wall.

FIG. 3*b* shows in a longitudinal sectional view the discharge gap formed by two coaxial cylinders with one circumferential multifunctional means arranged as dent protruding from the inner wall to the outer wall.

FIG. 4*a* shows in a longitudinal sectional view a discharge gap formed by two coaxial cylinders with one circumferential multifunctional means arranged as area of a different material in the outer wall.

FIG. 4*b* shows in a longitudinal sectional view a discharge gap formed by two coaxial cylinders with one circumferential multifunctional means arranged as area of a different material in the inner wall.

Figure 1:
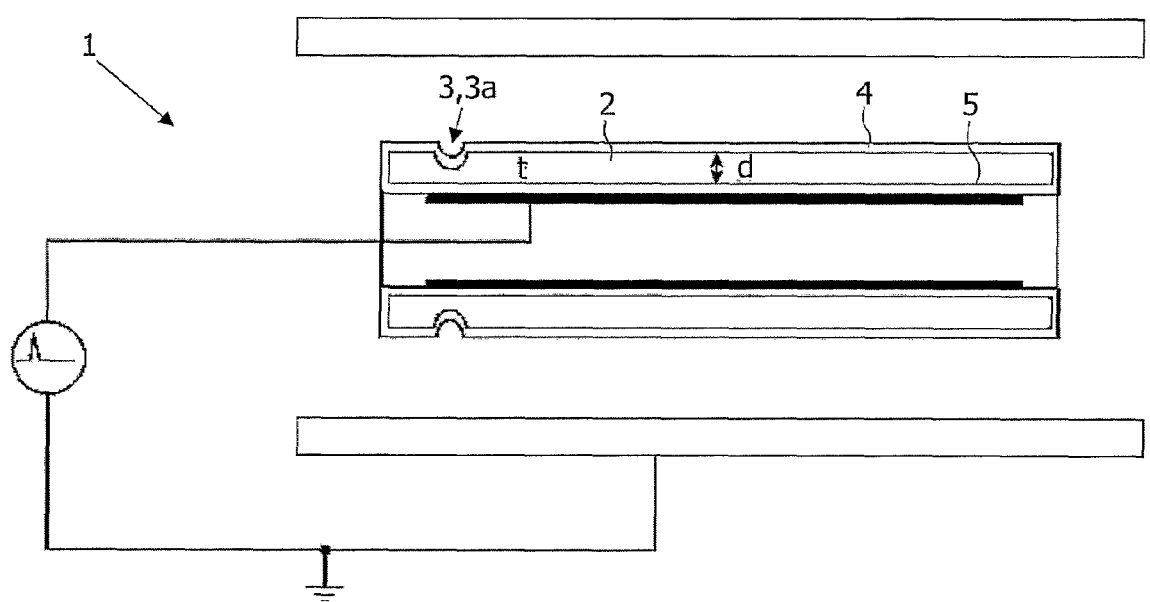

FIG. 1 shows a part of a DBD-lamp 1 including a discharge gap 2 formed by two coaxial cylinders with one integrated circumferential multifunctional means 3 arranged as an annular dent 3a protruding from the outer wall 4 to the discharge gap 2. The outer wall 4 and an inner wall 5, both form the discharge gap 2, are arranged toward each other with a constant distance d. In the area of the multifunctional means 3 the distance d of the discharge gap 2 is locally reduced by the dent 3a, having a distance t. This reduced distance d is the relevant distance determining the needed voltage for an ignition of the DBD-lamp. The wall thickness of the walls 4, 5 is about the wall thickness of the multifunctional means 3.

FIG. 2a-4b are showing embodiments of a coaxial DBD-lamp with differently arranged multifunctional means 3.

Figure 2A:
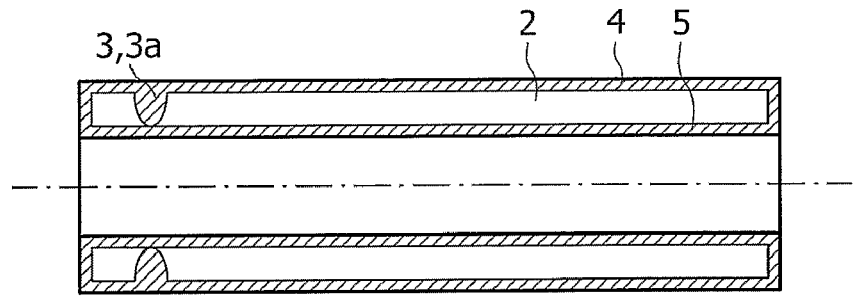

FIG. 2a shows in a longitudinal sectional view a discharge gap 2 formed by two coaxial cylinders, with one circumferential multifunctional means 3 arranged as thickening 3a protruding from the outer wall 4 to the inner wall 5. In this case the distance t of the multifunction means 3 equals d, which means that a direct contact between the inner and the outer wall is realized.

Figure 2B:
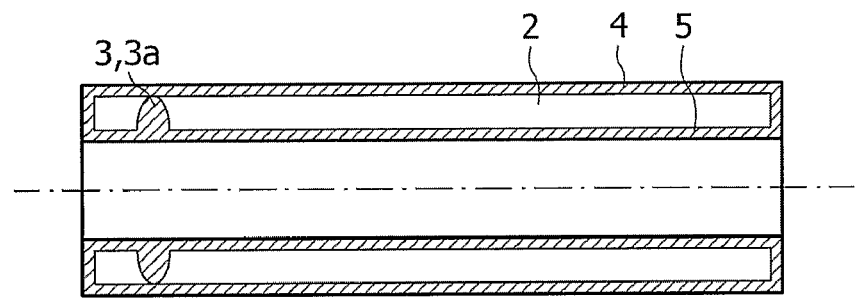
Figure 3A:
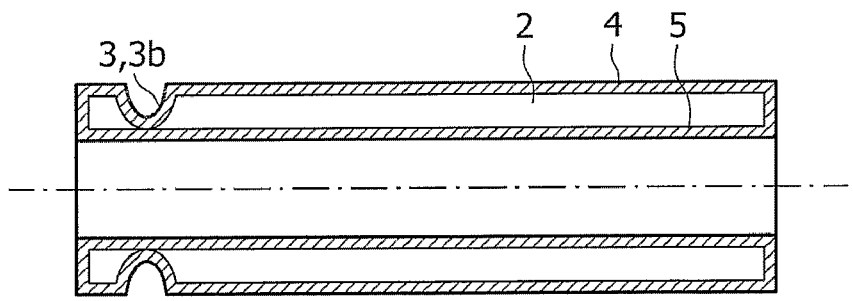

FIG. 2b shows in a longitudinal sectional view a discharge gap 2 formed by two coaxial cylinders with one circumferential multifunctional means 3 arranged as thickening 3a protruding from the inner wall 5 to the outer wall 4. Again, the distance t equals d, which means that a direct contact between the inner wall 5 and the outer wall 4 is realized FIG. 3a shows in a longitudinal sectional view a discharge gap 2 formed by two coaxial cylinders with one circumferential multifunctional means 3 arranged as dent 3b protruding from the outer wall 4 to the inner wall 5. As in FIGS. 2a and 2b the distance t equals d, which means that a direct contact between the inner and the outer wall is realized. The wall thickness of that multifunctional means 3 is less or equals the wall thickness of the outer wall 4.

Figure 3B:
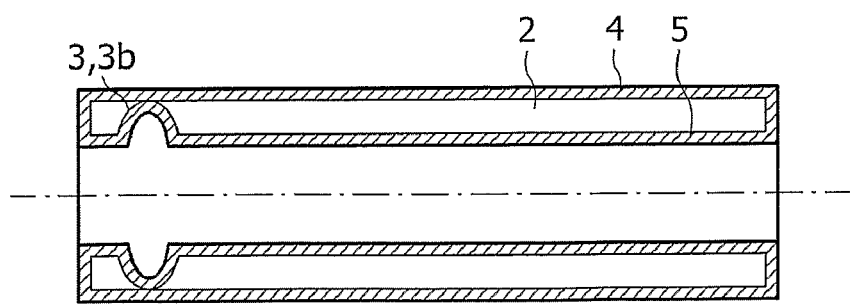

FIG. 3b shows in a longitudinal sectional view the discharge gap 2 of FIG. 1 formed by two coaxial cylinders with one circumferential multifunctional means 3 arranged as dent 3b protruding from the inner wall 5 to the outer wall 4. The wall thickness of that multifunctional means 3 is less or equals the wall thickness of the inner wall 5

Figure 4A:
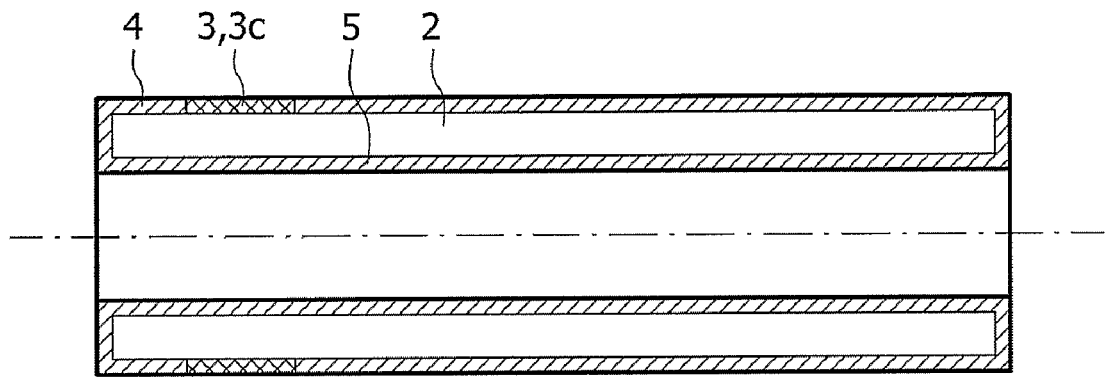

FIG. 4a shows in a longitudinal sectional view a discharge gap 2 formed by two coaxial cylinders with one circumferential multifunctional means 3 arranged as area of a different material 3c in the outer wall 4, compared to the material of the outer wall 4.

Figure 4B:
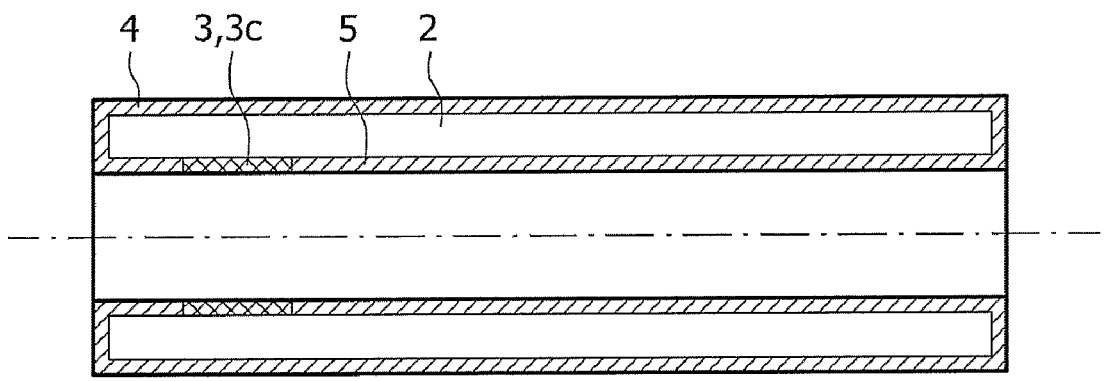

FIG. 4b shows in a longitudinal sectional view a discharge gap 2 formed by two coaxial cylinders with one circumferential multifunctional means 3 arranged as area of a different material 3c in the inner wall 5, compared to the material of the inner wall 5.

Figure 5:
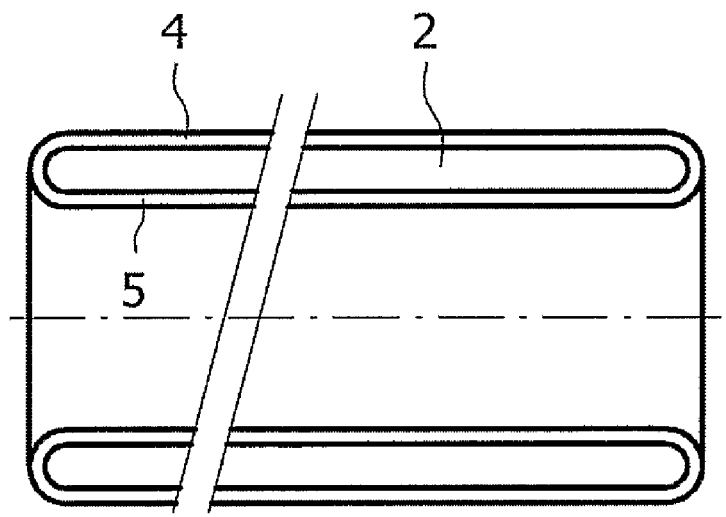
FIG. 5 shows schematic in a cross sectional view the structure of two cylinders forming a discharge gap.

FIG. 5 shows schematic in a cross sectional view the structure of two cylinders forming a discharge gap 2. The two cylinders are connected together, so that the outer cylinder forms the outer wall 4 and the inner cylinder forms the inner wall 5.

Figure 6:
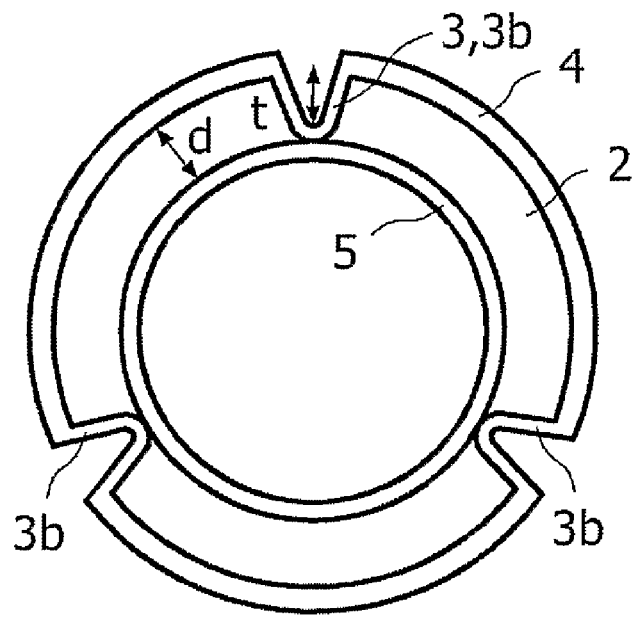
FIG. 6 shows schematic in a cross sectional view a section of coaxial constructed DBD-lamp having multifunctional means arranged as dent at the outer wall protruding to the discharge gap.

FIG. 6 shows schematic in a cross sectional view a section of coaxial constructed DBD-lamp with a discharge gap 2 and having multifunctional means 3 arranged as dents 3b at the outer wall 4 protruding towards the inner wall 5. The distance t equals the gap width d, so that the inner wall 5 contacts the outer wall 4 or rather the dents 3b.

Figure 7:
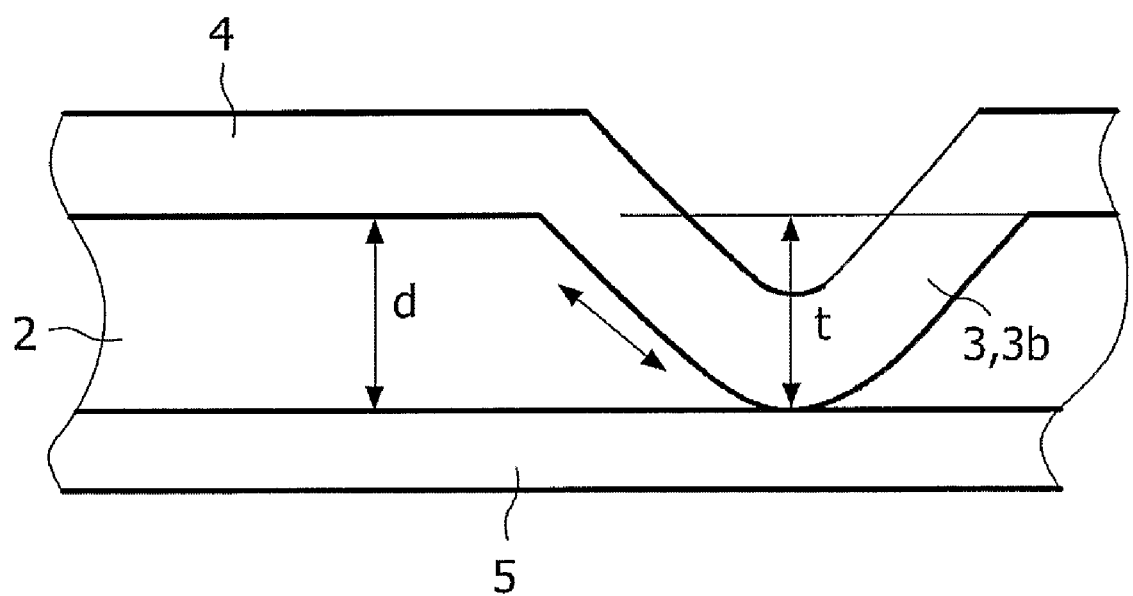
FIG. 7 shows in a schematic way a multifunctional means forming a direct contact in detail.

FIG. 7 shows schematic in a cross sectional view a section of coaxial constructed DBD-lamp having multifunctional means 3 arranged as dent 3b at the outer wall 4 protruding to and contacting the inner wall 5, so that d is about or equal t. The discharge happens along the inner surface of the outer wall 4, shown as arrow.

Figure 8A:
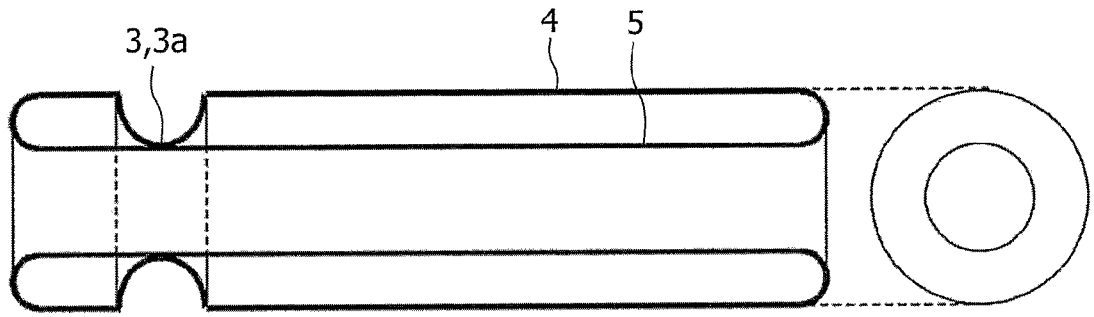
FIGS. 8a and 8b show in a schematic way the circumferential distribution of a multifunctional means of the DBD lamp.
Figure 8B:
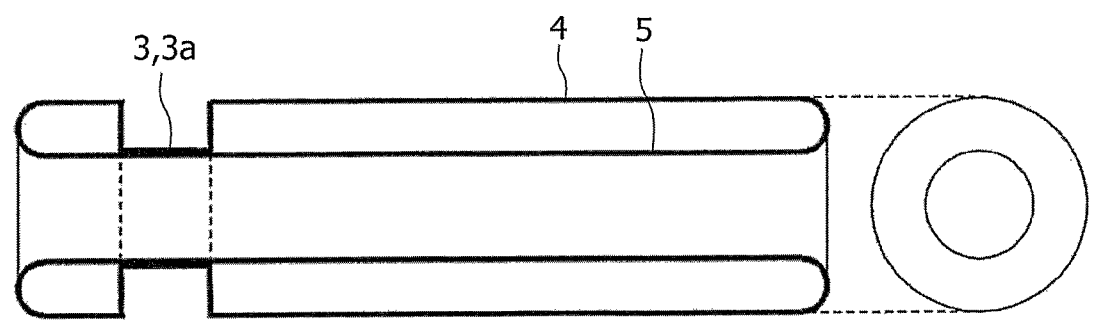

FIGS. 8a and 8b show the circumferential distribution of the multifunctional means (3, 3a). In FIG. 8a the multifunction means is distributed along a circumference line of the lamp. Instead of localized contact point(s) between inner and outer tube or inner and outer wall (4, 5), a (several) contact line(s) is (are) generated.

The contact line(s) may have any arbitrary shape along the inner and/or outer tube. Contact lines in parallel with the length axis of the lamp may have special advantages to provide a guidance aid, an ignition aid, and no modification of the cross sectional shape (vertical to the length axis of the lamp) is needed. The latter, is useful to provide a lamp without distortions for improved wiping.

In FIG. 8b the multifunction means (3, 3a) is distributed along a circumference area of the lamp. Instead of localized point(s) or line(s), a (several) contact area(s) is (are) generated.

The contact area(s) may have any arbitrary shape along the inner and/or outer tube or inner and/or outer wall (4, 5). Contact areas in parallel with the length axis of the lamp may have special advantages to provide a guidance aid, an ignition aid, and no modification of the cross sectional shape (vertical to the length axis of the lamp) is needed. The latter, is useful to provide a lamp without distortions for improved wiping.

List of Reference Numbers

| | |
|---|---|
| 1 | dielectric barrier discharge lamp (DBD lamp) |
| 2 | discharge gap |
| 3 | multifunctional means |
| 3 a | thickening |
| 3 b | dent |
| 3 c | area of different material |
| 4 | outer wall |
| 5 | inner wall |
| d | discharge gap width |
| t | distance (of the multifunctional means) |

The invention claimed is:

1. A dielectric barrier discharge lamp for generating and emitting an ultraviolet radiation comprising:
    an inner wall having a first inner surface, a first outer surface, and a first electrode associated with the inner wall;
    an outer wall having a second inner surface, a second outer surface, and a second electrode associated with the outer wall, wherein the outer wall is transparent or partly transparent;
    a cylindrical discharge gap formed between the inner wall and the outer wall, wherein the inner surface of the inner wall and the inner surface of the outer wall are facing the discharge gap, and wherein a filling is located within the discharge gap;
    two or more contacts, wherein a contact is a portion of the first inner surface of the inner wall touching a portion of the second inner surface of the outer wall, wherein the contact is formed by an integral portion of the inner wall and an integral portion of the outer wall;
    radiation generated by a gas discharge inside the discharge gap.

2. The dielectric barrier discharge lamp of claim 1, wherein the lamp has a coaxial lamp geometry, a dome lamp geometry, a flat lamp geometry, or planar lamp geometry.

3. The dielectric barrier discharge lamp of claim 1, wherein the lamp has a coaxial lamp geometry or a dome lamp geometry and the contacts are radially spaced apart.

4. The dielectric barrier discharge lamp of claim 1, wherein the contacts are point contacts.

5. The dielectric barrier discharge lamp of claim 1, wherein the contacts are tooth-like or sinus-like contacts.

6. The dielectric barrier discharge lamp of claim 1, wherein the contacts are formed as dents in the outer wall or the inner wall.

7. The dielectric barrier discharge lamp of claim 1, wherein the contacts are formed as thickenings in the outer wall or the inner wall.

8. The dielectric barrier discharge lamp of claim 1, wherein the contacts are line contacts.

9. The dielectric barrier discharge lamp of claim 1, wherein the contacts are area contacts.

10. The dielectric barrier discharge lamp of claim 1, wherein the inner wall and the outer wall are formed by two coaxial cylinder quartz tubes having an annular discharge gap between the inner wall and the outer wall.

11. The dielectric barrier discharge lamp of claim 1, wherein integral portion of the inner wall forming the contact is made from a material having a different electrical characteristic than the remainder of the inner wall.

12. The dielectric barrier discharge lamp of claim 1, wherein integral portion of the outer wall forming the contact is made from a material having a different electrical characteristic than the remainder of the outer wall.

13. A system for treating a surface, a solid, a liquid, or a gas comprising a dielectric barrier discharge lamp according to claim 1.

* * * * *